United States Patent [19]

Larsson

[11] 4,203,796
[45] May 20, 1980

[54] AN ARRANGEMENT FOR JOINING MATERIAL WEBS

[75] Inventor: Tore I. Larsson, Löddeköpinge, Sweden

[73] Assignee: Tetra Pak International AB, Lund, Sweden

[21] Appl. No.: 899,526

[22] Filed: Apr. 24, 1978

[30] Foreign Application Priority Data

Apr. 22, 1977 [SE] Sweden .............................. 7704647

[51] Int. Cl.² .......................................... B65H 19/08
[52] U.S. Cl. ................................. 156/504; 242/58.4; 242/58.5
[58] Field of Search ...................... 156/504, 505, 515; 242/58.4, 58.5

[56] References Cited

U.S. PATENT DOCUMENTS

| 1,724,225 | 8/1929 | Scott | 242/58.4 |
| 3,227,594 | 1/1966 | Ryan | 242/58.4 |
| 3,520,748 | 7/1970 | Reigger | 156/504 |
| 3,537,939 | 11/1970 | Delaplaine et al. | 156/504 |
| 3,654,035 | 4/1972 | Takimoto | 156/504 |
| 4,106,974 | 8/1978 | Hirsch | 156/504 |

Primary Examiner—Jerome W. Massie
Attorney, Agent, or Firm—Burns, Doane, Swecker & Mathis

[57] ABSTRACT

A method and apparatus for joining a new web of material to a moving web in a packing machine is disclosed. The beginning end of the new web is secured in a joining unit which is positioned over the moving web. The joining unit has a pivotably mounted cutting device which is actuated by a piston to cut the moving web. The operation of the joining unit is synchronized with that of the packing machine by a stationary cam over which a follower attached to the cutting device is displaced. When the moving web is about to run out, the joining unit is activated so that the moving web is cut off while the new web is automatically attached to the remaining running length by means of adhesive tape. The automatic joining unit eliminates the need to shut down operation of the packing machine when the web of material runs out.

5 Claims, 6 Drawing Figures

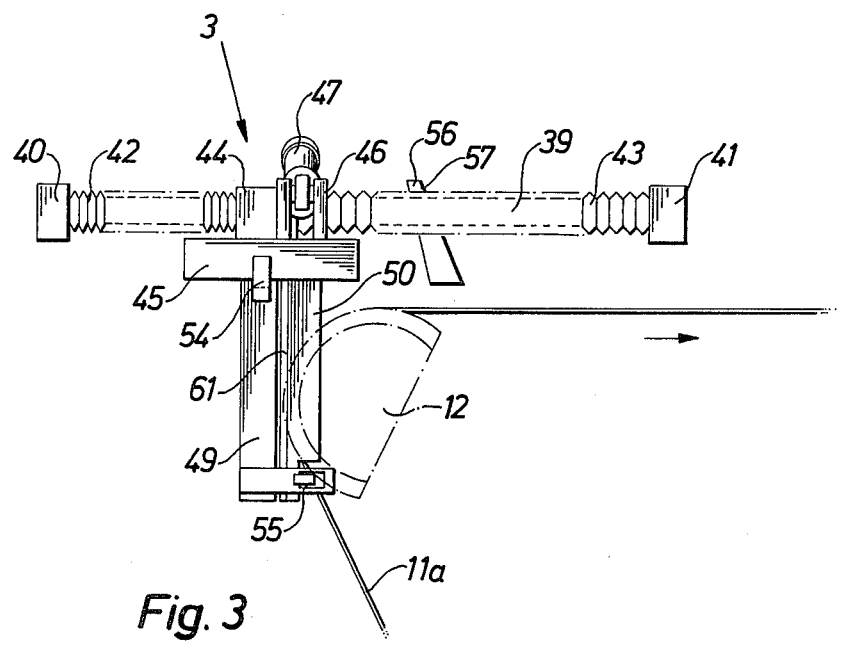
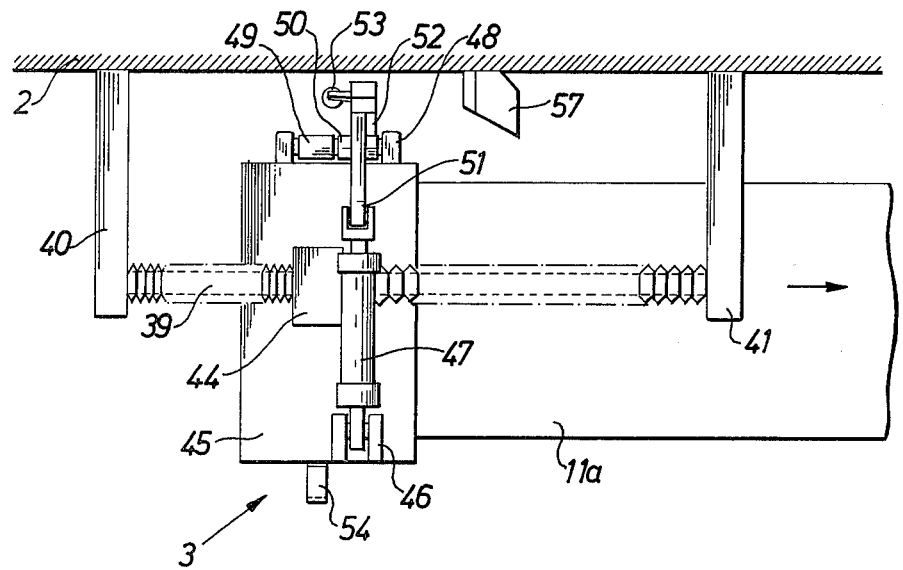

AN ARRANGEMENT FOR JOINING MATERIAL WEBS

The present invention relates to a method for joining together a first, moving material web with the starting end of a second material web.

The invention also relates to an apparatus for carrying out the method.

In machines which during operation consume a material web, an apparatus is required which makes possible the joining of a new material web to the material web which is being processed in the machine and which is at the point of running out. Machines which work intermittently and perhaps also with only one web at a time present no problem in this respect, and the joining arrangements can be accomplished very simply and the whole joining procedure may even be carried out manually. Continuously operating machines, which moreover process and consume several different material webs at the same time, make the joining a more difficult problem. This is true in particular for certain types of continuously operating packing machines which must not be stopped during the joining operation. In machines with two (or more) different material webs it also happens at odd times that the webs run out simultaneously which makes it necessary to provide automatic joining of at least one web. When several machines are in operation at the same time in one location, the automatic joining is necessary to allow the machines to be attended to by a minimum number of operators.

In known packing machines of the kind which use webtype packing material which is introduced into the machine in the form of magazine rolls, the joining up of a new roll is carried out primarily manually. However, in order to facilitate the work and to increase the precision, a mechanical means mounted on the packing machine is used. The mechanical means consists of a supporting surface with guides for the material webs which are to be joined together, a cutting device which is displaceable vertically to the material web and a device for the application of joining tape. In this joining arrangement it is assumed that the operator will assess in advance when a material web is at the point of finishing so that he is ready in good time to unwind the remaining length of web from the roll and join it to the starting end of the new material web which is introduced in the form of a full material roll. Even if the time required for the joining operation and the supply of the new material web is only a small part of the period during which a packing machine can operate before a new material web once more has to be introduced, it is easy to see that in the case of simultaneous operation of several packing machines (or of one packing machine which consumes a number of different material webs), sooner or later a situation will arise when several material webs will run out at the same time. In the case of the manual joining described it will then be necessary to stop the packing machine, which not only means diminished production but also brings about other disturbances in the form of incomplete and/or badly sealed packages, faulty levels of filling, loss of sterility, etc. It is generally desirable to avoid the abovementioned problems.

It is an object of the present invention to provide a method for the joining together of material webs, which method is not subject to the abovementioned disadvantages.

This object has been achieved in accordance with the present invention in that a method for joining together a first, moving material web with the starting end of a second material web has the characteristic that the starting end of the second material web is combined with a joining unit which subsequently is moved synchronously with the first material web while the latter is engaged by the joining unit. The first web is then cut so that, with the finishing end formed, it is combined and joined together with the starting end of the second material web. This method allows a rapid and accurate joining together of the packing material webs during operation of the machine, without the operator, apart from a certain amount of preparatory work, having to intervene in the joining procedure.

A preferred embodiment of the method in accordance with the invention has the further characteristic that the first material web is engaged and processed by means of a tool element whose movement controls the driving of the joining unit synchronously with the first material web. This makes possible a simple and functionally reliable advance of the joining unit at the same time as the movements of the tool element and the joining unit are synchronized with a high and consistent precision.

A further preferred embodiment of the method in accordance with the invention has the further characteristic that the joining together of the web ends takes place with the help of a tape strip which has been applied previously to the starting end of the second material. The method to achieve the actual joining together with the help of a tape strip has proved to be very reliable and does not involve any problem for the operator, since the tape strip can be applied to the starting end of the second material web in good time before the joining operation.

It is a further object of the present invention to provide an apparatus for carrying out the method described above. The apparatus, while of a simple design and high operational safety, makes possible the automatic joining together of two material webs.

This object has been achieved in accordance with the invention in that an apparatus for the joining together of a first, moving material web with the starting end of a second material web has the characteristic that the apparatus has a joining unit which is displaceable along part of the travel of the first material web. The apparatus supports a clamping tool for the clamping fast of the starting end of the second material web and a combined cutting and joining tool for the cutting of the first material web and the pressing together and joining of the finishing end of the first material web and the starting end of the second material web. Using the construction just described with a joining unit which is displaceable synchronously with the moving material web, the processing of the web and the joining can take place without any break in the operation.

A preferred embodiment of the apparatus in accordance with the invention has the further characteristic that the joining unit is displaceable between a rest position and a working position in which it is situated directly adjacent the first material web.

A further characteristic of the apparatus in accordance with the invention is that the joining unit is supported by, and is displaceable along, a guide bar, part of which extends parallel with, and adjoining, the first material web.

A further characteristic of the apparatus in accordance with the invention is that the joining unit includes a displaceable plate which pivotally supports the clamping tool as well as the cutting tool, each of which by itself is pivotable between an inactive position and an active position when it is in contact with the underside of the plate.

A further characteristic of a preferred embodiment of the apparatus in accordance with the invention is that the cutting tool is located parallel with, and adjoining, the clamping tool and is provided with a cutting edge cooperating with the clamping tool.

A further preferred embodiment of the apparatus in accordance with the invention has the further characteristic that it includes a driving element for the actuation of the cutting tool. The driving element during actuation of the tool to its active position is adapted so that through engagement with a stationary cam surface the driving element displaces the joining unit synchronously with the movement of the first material web. Using the same driving device actuating the cutting tool as well as the joining unit in a mechanically combined relation, a very high precision and synchronization of the movements is ensured.

Finally, a further preferred embodiment of the apparatus in accordance with the invention has the characteristic that the cutting tool at its bearing end supports a pulley which co-operates with the stationary cam surface during pivoting from the inactive to the active position.

BRIEF DESCRIPTION OF THE DRAWINGS

The present invention will be described with reference to the accompanying drawings, in which like members bear like reference numerals and in which:

FIG. 2 shows a side view on a larger scale of the arrangement in accordance with the invention, the arrangement being in its rest position.

FIG. 3 shows the arrangement in accordance with FIG. 2 seen from above.

DETAILED DESCRIPTION OF THE PREFERRED EMBODIMENT

Figure 1:
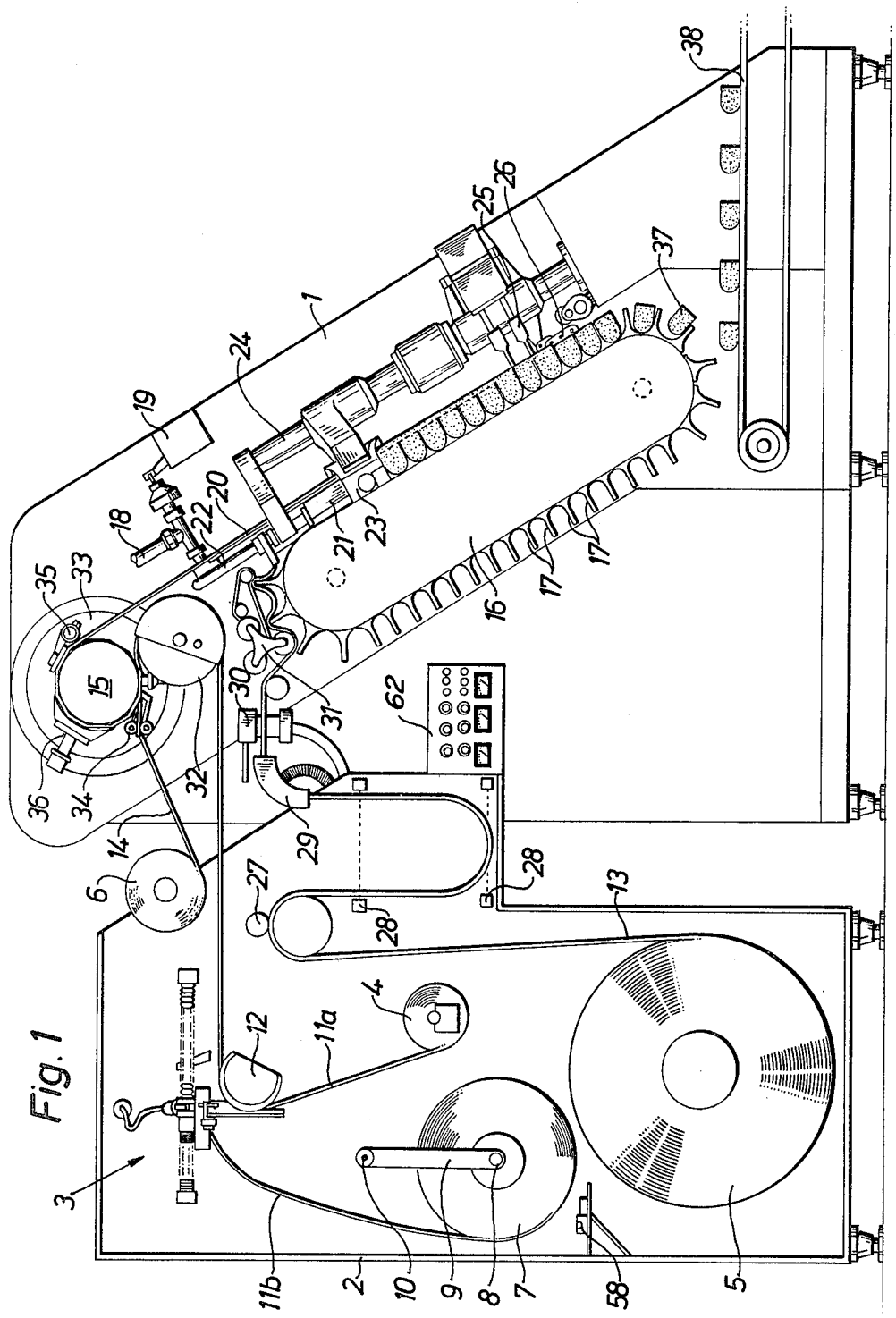
FIG. 1 shows a side view of an arrangement in accordance with the invention on a packing machine of known design, wherein only the parts essential for the understanding of the invention have been included.
Figure 4:
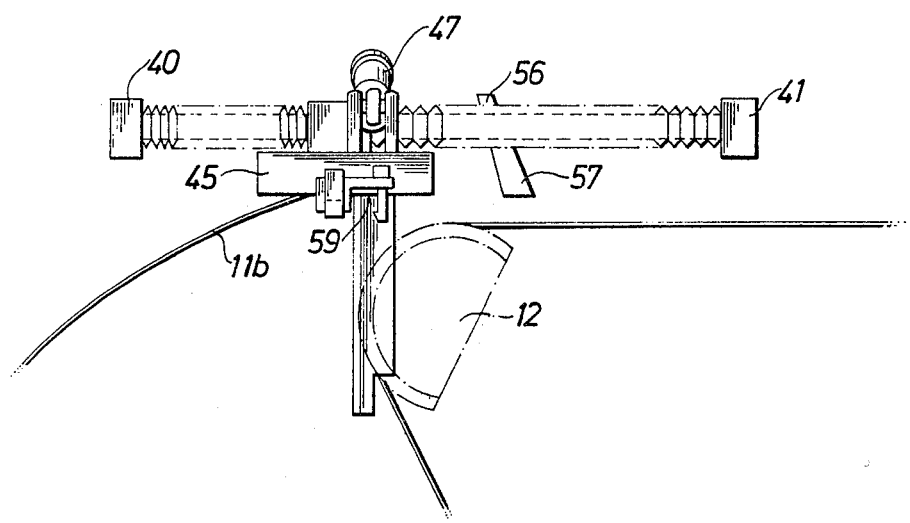
FIG. 4 shows the arrangement in accordance with the invention during preparation for the joining, which position corresponds to that shown in FIG. 1.

With reference to FIG. 1 a front elevation of a packing machine comprising a joining unit in accordance with the invention is shown. The packing machine section proper has been given the reference numeral 1, a packing material section has been indicated by reference numeral 2 and the joining unit in accordance with the invention is indicated schematically by reference numeral 3.

The known packing machine manufactures filled and closed packages from a web-type material which is supplied from material rolls 4, 5 and 6, all of which are mounted so that they can rotate in the packing material section 2 of the machine. In the packing material section 2 is also included a packing material roll 7 which is intended to replace the roll 4 when the latter runs out of packing material. The roll 7 is suspended so that it can rotate around an axle 8 which via lever arms 9 (only one shown on drawing) is connected to and is pivotable about an axle 10 which is in a fixed position in the packing material section 2.

From the packing material roll 4 the packing material web 11a is conducted via a guide element 12 to the main section 1 of the packing machine where, together with the material web 13 wound off the packing material roll 5, it is converted to filled packing containers. The two material webs 11a and 13 may consist, for example, of extruded foamed plastic webs of polystyrene material covered on both sides by layers of homogeneous polystyrene. The magazine roll 6 contains strip material 14 of homogeneous plastic material which is intended for use as a removable cover material over the emptying holes in the finished packing containers.

The packing machine proper consists, as mentioned above, of a frame 1 which in its upper part supports a rotating drum 15 over which passes the packing material web 11a, and where a number of operations are carried out in stations along the periphery of the drum. The packing machine further includes an arrangement 16 for the moulding of the web 13. The arrangement 16 comprises movable moulds 17 which are fitted to an endless chain in the figure shown moves in clockwise direction. In FIG. 1 is also shown a supply line 18 which from a reservoir (not shown) conducts the material to be filled into containers to the packing machine. The amount of contents supplied is controlled with the help of a control valve 19 which allows the desired amount of contents to pass to the packages via a filler pipe 20 which extends along the chain of movable moulds 17. Directly adjacent to and partly surrounding the mould chain a heating device 21 is provided which receives air from a compressor or the like via a line 22. The heating device 21 and a folding device 23 are supported by a guide bar 24 aligned parallel to the mould chain. The heating device 21 as well as the folding device 23 can be displaced in a forwards and backwards movement along the guide bar. Below the heating device 21 and the folding device 23 a sealing device 25 and a cutting device 26 are also provided, the first mentioned likewise being displaceable in a forward and backward movement along the guide bar 24. The movement is adapted so that the units move synchronously with the moulds 17 during the downward movement of the same, whereas the return movement of the units upwards is faster.

The packing machine operates in the following manner:

A packing material web 13 provided with crease lines is rolled off the magazine roll 5. The packing material web 13 is rolled off with the help of a driving roll 27, whose rotation in a known manner is controlled with the help of two photocell devices 28 which monitor the length of a slack loop of packing material. After the photocell unit the material web 13 passes two heating device 29 and 30 and a moulding unit 31 by means of which the heated and thus softened packing material is brought into contact with the moulds 17 of the forming arrangement 16. The moulds 17 are arranged in the form of an endless chain which moves in a closed track around the forming arrangement 16. With the help of the moulding device 31 the packing material web 13 is made to adapt itself against the moulds 17, which means that the material web 13 is shaped to form an endless row of U-shaped parts which with the help of the forming arrangement 16 are made to move at a constant speed substantially downwards along the processing side of the forming arrangement 16, that is to say, the side in FIG. 1 facing towards the right.

The second packing material web 11a is rolled off its magazine roll 4 and is led via the guide element 12 arranged directly underneath the joining device 3 to a guide roll 32 whereupon the material web 11a is made to make contact with the feed drum 15. The latter, as mentioned previously, is provided with a number of sections or form surfaces, each of which has a width which largely corresponds to the distance between two successive moulds 17 on the forming arrangement 16. The feed drum 15 rotates at a constant speed while an outer rim or oscillator plate 33 moves in a reciprocating driving movement around the drum 15. The plate 33 carries processing devices such as a hole punching and cover strip applying device 34, a forming and cutting device 35 and a heating device 36. When the web 11a with the help of the feed drum 15 is conducted past the processing stations 34–36, the punching of the emptying hole, the attachment of cover strips 14 over the emptying hole, the heating and possibly thermoforming of the web and the cutting off of the edge zones of the web substantially perpendicular to the longitudinal direction of the web are carried out in the processing stations 34–36. As a result the edge zones of the web are converted largely to projecting tabs following one another whose length substantially corresponds to the height of the moulds 17. The web is fed with the help of the feed drum 15 at a speed which corresponds to the speed of movement of the moulds, the web 11a being advanced until its central part is located over the tops of the moulds 17, while the web edges converted to tabs or lugs project outside the moulds. When the web 11a with the help of the feed drum 15 is fed synchronously with the movement of the moulds 17, the units displaceable along the guide bar 24 reach an upper limit position and commence a downwards movement which is also synchronous with the movement of the moulds 17. By means of the heating device 21 hot air is blown against the underside of the edge regions or tabs of the web 11a, which causes the plastic material to soften and be prepared for sealing. At the same time the edges of the web 13 are also warmed up due to hot air being blown against the web edge regions exposed at the side edges of the moulds.

At the same time as the areas of the webs 11a and 13, which are intended to be sealed to one another, are warmed up by means of the heating unit 21, the tabs or lugs of the web 11a, heated during the previous operating stage, are folded down by means of the folding device 23 to rest against the edge zones of the web 13 situated outside the side edges of the moulds which have likewise been heated. In this way, the portions of the webs placed together are sealed to one another to form a mechanically consistent and lasting seal. When the webs 11a and 13 have been combined with one another through the side sealing operations described above, the material to be filled into the containers is supplied through the filler pipe 20 which is arranged below the web 11a but above the tops of the moulds 17, the compartment-like spaces formed underneath the web 11a being filled with the intended contents. The spaces are subsequently sealed off by means of the sealing device 25 to form closed units in that the central part of the web 11a is sealed to the parts of the web 13 which lie over the tops of the upright parts of the moulds 17. The sealing devices 25 participate in the upward and downward movement which means that the sealing takes place while the unit moves downwardly in synchronization with the moulds. The closed packing units formed by the packing machine are finally separated from one another with the help of the cutting device 26 which separates the units from each other with a cut through the sealing zones produced with the help of the sealing device 25. The filled and closed packing units 37 are then transferred at the bottom end of the mould chain to a conveyor 38 so as to be removed and possibly to be packed in boxes or the like.

The packing machine is actuated by means of a control and instrument panel 62 which contains the required control elements as well as instruments indicating the temperature in different heating zones, etc.

After this description of the packing machine and its function, the joining unit in accordance with the invention mounted on the packing machine will be described in more detail together with the joining method in accordance with the invention. The joining unit in accordance with the invention is shown in FIG. 1 fitted to the upper part of the packing machine section 2 and indicated by reference numeral 3. The detailed description of the joining unit and its function will be described with reference to FIGS. 2–6, in which the joining unit is shown on a larger scale in different stages during the joining procedure.

FIGS. 1 and 3 indicate that the joining unit is supported by and is displaceable along a guide bar 39, which via two brackets 40 and 41 is firmly fixed to the packing machine material frame 2. The guide bar 39 is arranged horizontally and extends along a part of that portion of the packing material web 11a which passes from the guide element 12 to the guide pulley 32 on the processing section of the packing machine (FIG. 1). The guide bar 39 is protected by two bellows-type protecting elements 42 and 43 which extend between the brackets 40, 41 respectively and the bearing cap 44, by means of which that part of the joining unit which is supported is displaceable along the guide bar. The bellows-type protective elements completely cover the guide bar 39 and are manufactured, moreover, of a springy material, so that they also serve as springs which serve to displace the movable part of the joining unit to and retain it in the rest position shown in FIGS. 2 and 3.

The displaceable part of the joining unit, which has been indicated by reference numeral 3, consists of a base plate 45 which is suspended under the guide bar 39 and is retained by means of the bearing cap 44 mentioned earlier. On the upper side of the base plate 45 there is in addition to the bearing 44 an attachment 46 for the pivotable mounting of one end of a pneumatic piston and cylinder unit 47 which extends substantially perpendicular to and over the guide bar 39 in the direction towards the wall of the machine from which project the two brackets 40 and 41.

On the side edge of the base plate 45 facing towards the machine wall is provided a further attachment 48 which includes two brackets projecting from the base plate and an axle extending between them which runs parallel with the guide bar 39 and serves for the pivotable mounting of two tools arranged adjacent one another, namely a clamping tool 49 and a cutting tool 50. The cutting tool is provided on its side facing towards the clamping tool 49 with a cutting edge 61 which in co-operation with the adjoining clamping tool has a scissor-type function. The two tools 49 and 50 are each individually pivotable between a free position wherein they hang parallel downwards, as shown in FIGS. 2 and 3, and a position wherein they are parallel and in contact with the underside of the base plate 45. The pivoting of the clamping tool 49 takes place manually, whereas the cutting tool 50 is actuated by means of the piston and cylinder unit 47, the piston rod of which is connected via a transmission element 51 to a lever 52 projecting from the bearing sleeve of the cutting tool 50. The lever 52 is provided on its side facing the adjoining clamping tool 49 with a freely rotating pulley 53.

For the retaining of the clamping tool 49 in the described position in contact with the underside of the base plate 45, the base plate is provided on the opposite side in relation to the bearing unit 48 with a locking device 54 which is arranged to engage automatically with the clamping tool 49 and retain the latter in its working position in contact with the base plate 45. The clamping tool 49 supports on its outer free end a locking device 55 projecting in lateral direction which is adapted to engage with the outer free end of the cutting tool which will be described in more detail in the following.

Finally, the joining unit in accordance with the invention includes an element 56 connected to the machine frame which has a cam surface 57 extending downwards and to the right in FIG. 2, that is to say, in the same direction as the direction of travel of the part of the material web 11a parallel with the guide bar 39. The angle of the cam surface 57 in relation to the vertical plane is variable so as to be adaptable to the speed of the packing material web 11a, the number of strokes per minute of the piston and cylinder unit 47, and like variables.

The manner of operation of the arrangement will now be described in more detail starting from the rest position which is shown in FIGS. 2 and 3. In the rest position there is no action upon the piston and cylinder unit 47, that is to say, the piston rod is in the position shown on the drawing, which means that the cutting tool 50 extends vertically downwards. In the absence of outside forces the freely pivoting clamping tool 49 also hangs vertically downwards side by side with the cutting tool. In this position the two tools are in a vertical plane situated between the material web 11a and the machine wall supporting and joining unit and the unit can thus be displaced along the guide bar 39 without the tools coming into contact with the material web.

Figure 5:
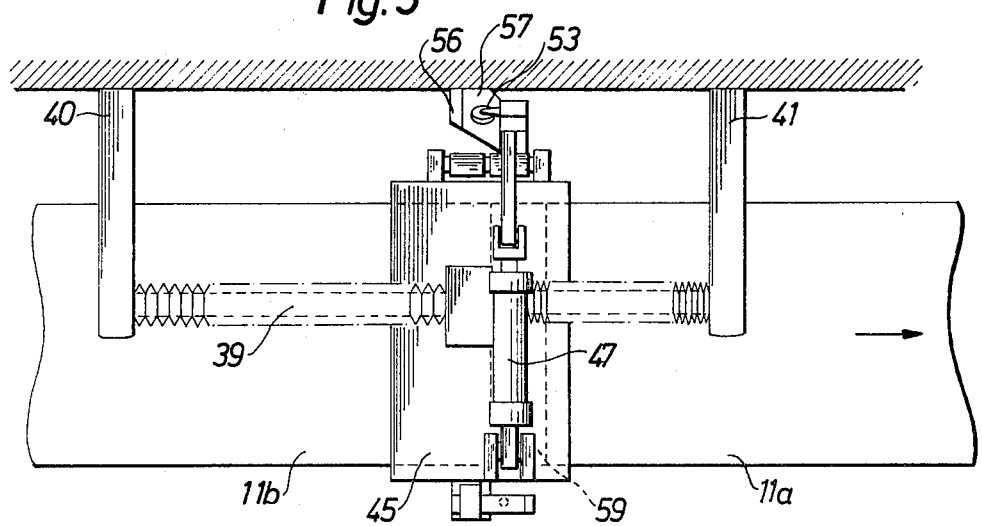
FIG. 5 shows the arrangement seen from above and in working position.

When the material roll 4 from which the material web 11a runs off commences to diminish in circumference to such an extent that the attachment of a new web is likely to become necessary within a short time, a new material roll 7 of the same kind is suspended in the suspension arrangement 8-10. The material web 11b of the new material roll 7 is then cut off at a right angle relative to the longitudinal direction of the material web and is provided with a strip of joining tape which is applied in such a manner along the rectangular cut that half the width of the tape strip is placed outside the end of the material web. The cutting off and application of tape may be carried out with the help of a unit 58 (FIG. 1) which is designed in a known manner and comprises a knife as well as a tape applicator. After the cutting off of the end of the web and the application of the tape strip the material web 11b is taken up to the joining unit 3, where the end of the material web is positioned against the underside of the base plate 49 while the clamping tool is pivoted manually upwards so that the web is locked in this position with the help of the locking device 54. In this way the end of the material web 11b is secured between the plate 45 and the clamping tool 49. The web end has been placed so that the tape strip (59 in FIG. 5) projects outside the clamping jaw 49 (towards the right in FIG. 5) and the side coated with adhesive faces downwards. To facilitate the introducing of the end of the material web 11b at the correct angle between the clamping tool 49 and the plate 50 it is appropriate to provide the material end simultaneously with the rectangular cutting-off in the unit 58 with a transverse crease line which on correct introduction of the web end underneath the clamping tool 49 should coincide with the edge line of the clamping tool remote from the cutting tool 50. After the end of the material web 11b has been secured in the displaceable joining unit 3 (FIG. 4) the unit is displaced manually in the direction of movement of the web 11a to the position which is shown in FIG. 5, where the pulley 53, located at the rear end of the cutting jaw 50, is positioned against the upper end of the sloping cam surface 57 of the stationary device 56. The unit is then virtually above the portion of the material web 11a coming from the guide device 12 and the arrangement is ready for automatic joining.

Figure 6:
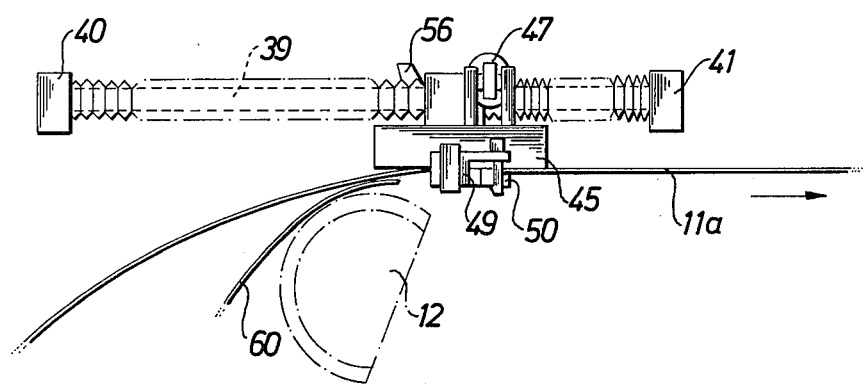
FIG. 6 shows the arrangement in accordance with the invention at the moment of joining.

The joining procedure itself can be initiated either manually or it can be controlled by a photocell, not shown on the drawing, which monitors the moving web 11a and gives a signal for joining when the finishing end of the web leaves the roll 4. When the joining procedure is initiated, a valve (not shown) opens the supply of compressed air to the pneumatic piston and cylinder unit 47, with the consequence that the piston rod projects from the cylinder, and via the transmission link 51 acts upon the lever arm 52 projecting from the rear end of the cutting tool 50. This has the result that the cutting tool 50 will be acted upon and start to pivot about its point of support in the direction towards the underside of the plate 45. This pivoting of the cutting tool causes the pulley 53, arranged at the rear end of the jaw, to simultaneously commence moving downwards along the sloping cam surface 57, the displaceable cutting unit 3 coming to be displaced parallel to the material web 11a and at a speed which fully corresponds to the rate of movement of the web. After a certain pivoting angle, the cutting tool 50 will come to rest against the underside of the material web 11a and on continued pivoting a cutting off of the material web will occur by virtue of the co-operation between the cutting edge 61 of the cutting tool and the opposite edge of the clamping tool 49 situated in contact with the underside of the plate 45. Under the continued effect of the piston and cylinder unit 47 the cutting tool 50 finally presses the rectangular end edge of the material web 11a to make contact with the adhesive layer of the tape strip 59, thus completing the joining together of the finishing end of the outgoing material web 11a and the starting end of the new material web 11b. When the cutting tool 50 has attained this position it releases the locking device 55 of the clamping tool 49 at the same time as the piston movement of the cylinder unit 47 is reversed, which means that the locking device 54 is acted upon and releases the clamping tool 49 so that the cutting tool 50 returns to its vertical position taking the clamping tool 49 with it. In other words, the material web 11a, 11b thus joined together is released immediately after joining from the joining unit 3 and can run without any obstruction from the material roll 7 via the guide element 12 and to the processing part of the machine. The residual end bit of the running out material web, marked 60 in FIG. 6, is subsequent manually removed at the same time as the empty material roll 4. After manual resetting of the displaceable joining unit 3 to the position shown in FIG. 2 the arrangement is once more ready for joining and the described procedure can be repeated.

The arrangement described, like the method described can of course be modified in certain parts, e.g. in that certain manual stages are automated. The principle of operation described, however, has been found to function well and to offer a number of advantages. Thus it is possible with the simple and reliable arrangement described to carry out a safe joining without an unnecessary waste of material. The previously frequently encountered problem of several material webs running out at the same time, which made necessary a shutting down of the machine for joining, has been completely eliminated, and the production capacity of the machine has thereby been appreciably increased.

I claim:

1. An apparatus for joining a first web of material with a second web of material comprising:

means for longitudinally advancing the first web;

holding means for positioning a starting end of the second web relative to the first web during movement of the first web;

cutting means for cutting the first web at a predetermined location;

splicing means for carrying said holding means and said cutting means, said splicing means being located adjacent to the first web and displaceable in the longitudinal direction of travel of the first web, and said holding means and cutting means including first and second members, respectively, pivotably mounted on said splicing means such that said members having corresponding and cooperating cutting edges which sever the first web at a predetermined location upon pivoting the second member; and means for synchronizing the displacement of said splicing means with the longitudinal advancement of the first web, said synchronizing means including a stationary cam surface with a follower member carried by said cutting means, said follower member engaging the cam surface during a pivoting of said pivotably mounted member of the cutting means.

2. The apparatus of claim 1 wherein said splicing means is displaced between a first position whereat the second web is secured to the holding means and a second position whereat the second web is joined to the first web.

3. The apparatus of claim 1 further comprising guide means for carrying said splicing means, said guide means including a guide bar extending parallel to the longitudinal direction of travel of the first web.

4. The apparatus of claim 1 wherein said splicing means includes plate means for supporting the first and second webs during the joining together of the webs.

5. The apparatus of claim 1 further comprising actuating means for driving said cutting means, said actuating means being adapted to engage said cam surface with said follower member to synchronize the position of the splicing means with the first web.

* * * * *